(12) United States Patent
Cann et al.

(10) Patent No.: US 7,148,348 B2
(45) Date of Patent: Dec. 12, 2006

(54) PROCESS FOR PREPARING PYRROLOTRIAZINE ANILINE COMPOUNDS USEFUL AS KINASE INHIBITORS

(75) Inventors: Reginald O. Cann, Middletown, CT (US); Edward J. Delaney, Princeton, NJ (US); Junying Fan, Monmouth Junction, NJ (US); Luca Parlanti, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/199,746

(22) Filed: Aug. 9, 2005

(65) Prior Publication Data

US 2006/0035886 A1    Feb. 16, 2006

Related U.S. Application Data

(60) Provisional application No. 60/600,935, filed on Aug. 12, 2004.

(51) Int. Cl.
C07D 487/04    (2006.01)
A61K 31/53    (2006.01)
A61P 19/02    (2006.01)

(52) U.S. Cl. ...................... 544/183; 514/243
(58) Field of Classification Search ................ 544/183
See application file for complete search history.

(56) References Cited

U.S. PATENT DOCUMENTS

| | | | |
|---|---|---|---|
| 4,200,750 A | 4/1980 | Warner, Jr. et al. |
| 4,908,056 A | 3/1990 | Tseng |
| 5,658,903 A | 8/1997 | Adams et al. |
| 5,686,457 A | 11/1997 | Traxler et al. |
| 5,932,576 A | 8/1999 | Anantanarayan et al. |
| 5,945,418 A | 8/1999 | Bemis et al. |
| 5,977,103 A | 11/1999 | Adams et al. |
| 6,087,496 A | 7/2000 | Anantanarayan et al. |
| 6,130,235 A | 10/2000 | Mavunkel et al. |
| 6,147,080 A | 11/2000 | Bemis et al. |
| 6,251,914 B1 | 6/2001 | Adams et al. |
| 6,277,989 B1 | 8/2001 | Chakravarty et al. |
| 6,518,269 B1 | 2/2003 | Camden et al. |
| 6,589,947 B1 | 7/2003 | Hamanaka et al. |
| 6,670,357 B1 | 12/2003 | Leftheris et al. |
| 6,867,300 B1 | 3/2005 | Godfrey, Jr. et al. |
| 6,869,952 B1 | 3/2005 | Bhide et al. |
| 6,900,217 B1 | 5/2005 | Chen |
| 6,906,067 B1 | 6/2005 | Moriarty et al. |
| 6,908,916 B1 | 6/2005 | Mastalerz et al. |
| 6,916,815 B1 | 7/2005 | Vite et al. |
| 6,933,386 B1 | 8/2005 | Bhide et al. |
| 6,951,859 B1 | 10/2005 | Bhide et al. |
| 6,962,915 B1 | 11/2005 | Das et al. |
| 6,969,717 B1 | 11/2005 | Bhide et al. |
| 6,982,265 B1 | 1/2006 | Hunt et al. |
| 2001/0041673 A1 | 11/2001 | Fossa |
| 2002/0065270 A1 | 5/2002 | Moriarty et al. |
| 2003/0139435 A1 | 7/2003 | Ahmed et al. |
| 2003/0232831 A1 | 12/2003 | Dyckman et al. |
| 2003/0232832 A1 | 12/2003 | Lombardo et al. |
| 2004/0082582 A1 | 4/2004 | Dyckman et al. |
| 2004/0157846 A1 | 8/2004 | Chen et al. |
| 2004/0229877 A1 | 11/2004 | Leftheris et al. |
| 2005/0043306 A1 | 2/2005 | Leftheris et al. |
| 2005/0124621 A1 | 6/2005 | Bhide et al. |
| 2005/0143398 A1 | 6/2005 | Das et al. |
| 2005/0182058 A1 | 8/2005 | Fink et al. |
| 2005/0197339 A1 | 9/2005 | Gavai |

(Continued)

FOREIGN PATENT DOCUMENTS

EP    0 713 876    5/1996

(Continued)

OTHER PUBLICATIONS

Chemical Abstracts, vol. 88, No. 121113q, p. 541 (1978).

(Continued)

*Primary Examiner*—Venkataraman Balasubramanian
(74) *Attorney, Agent, or Firm*—Joseph C. Wang; Burton Rodney

(57) ABSTRACT

A process is provided for the process for preparing a pyrrolotriazine aniline p38 kinase inhibitor such as amide II

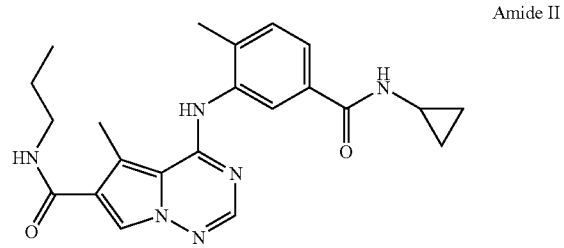

Amide II by the direct aminolysis of the ester I

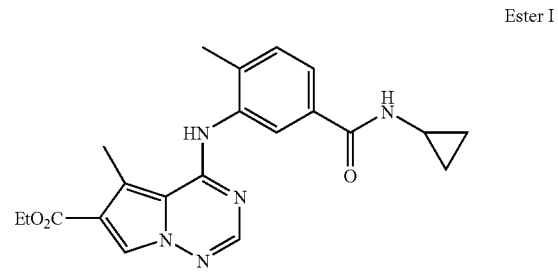

Ester I wherein ester I is reacted with a strong organometallic base, such as hexyllithium or n-butyllithium and the desired amine such as n-propylamine to form the amide II.

11 Claims, No Drawings

U.S. PATENT DOCUMENTS

| | | |
|---|---|---|
| 2005/0209454 A1 | 9/2005 | Swaminathan et al. |
| 2005/0245530 A1 | 11/2005 | Borzilleri et al. |
| 2006/0003967 A1 | 1/2006 | Shi et al. |
| 2006/0004006 A1 | 1/2006 | Borzilleri et al. |
| 2006/0009454 A1 | 1/2006 | Cai et al. |
| 2006/0014745 A1 | 1/2006 | Gavai et al. |
| 2006/0019928 A1 | 1/2006 | Lin et al. |

FOREIGN PATENT DOCUMENTS

| | | |
|---|---|---|
| EP | 0 795 556 | 9/1997 |
| EP | 0 778 277 | 6/2003 |
| WO | WO 98/08847 | 3/1998 |
| WO | WO 99/24033 | 5/1999 |
| WO | WO 00/12074 | 3/2000 |
| WO | WO 00/12497 | 3/2000 |
| WO | WO 00/20402 | 4/2000 |
| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |
| WO | WO 01/47897 | 7/2001 |
| WO | WO 02/40486 | 5/2002 |
| WO | WO 03/002542 | 1/2003 |
| WO | WO 03/002544 | 1/2003 |
| WO | WO 03/042172 | 5/2003 |
| WO | WO 03/091229 | 11/2003 |
| WO | WO 2003/090912 | 11/2003 |
| WO | WO 2003/090912 A1 * | 11/2003 |
| WO | WO 03/099286 | 12/2003 |
| WO | WO 2004/009542 | 1/2004 |
| WO | WO 2004/009601 | 1/2004 |
| WO | WO 2004/009784 | 1/2004 |
| WO | WO 2004/013145 | 2/2004 |
| WO | WO 2004/043912 | 5/2004 |
| WO | WO 2004/054514 | 7/2004 |
| WO | WO 2004/072030 | 8/2004 |
| WO | WO 2005/042537 | 5/2005 |
| WO | WO 2005/058245 | 6/2005 |
| WO | WO 2005/065266 | 7/2005 |
| WO | WO 2005/066176 | 7/2005 |

OTHER PUBLICATIONS

Connolly, D.T. et al., "Human Vascular Permeability Factor", The Journal of Biological Chemistry, vol. 264, No. 33, pp. 20017-20024 (1989).

Cullinan-Bove, K. et al., "Vascular Endothelial Growth Factor/Vascular Permeability Factor Expression in the Rat Uterus: Rapid Stimulation by Estrogen-Induced Increases in Uterine Capillary Permeability and Growth", Endocrinology, vol. 133, No. 2, pp. 829-837 (1993).

de Vries, C. et al., "The fms-Like Tyrosine Kinase, a Receptor for Vascular Endothelial Growth Factor", Science, vol. 255, pp. 989-991 (1992).

Eskins, F., "Angiogenesis inhibitors in clinical development; where are we now and where are we going?", British Journal of Cancer, vol. 90, No. 1, pp 1-7 (2004).

Ewald, H. et al., "Reactions of 1,2,4-Triazines with Dimethyl Acetylenedicarboxylate", Liebigs Ann. Chem., pp. 1718-1724 (1977).

Fabbro, D. et al., "Protein kinases as targets for anticancer agents: from inhibitors to useful drugs", Pharmacology & Therapeutics, vol. 93, pp. 79-98 (2002).

Fan, T.-P.D. et al., "Controlling the vasculature: angiogenesis, antiangiogenesis and vascular targeting of gene therapy", Trends in Pharmacological Sciences, vol. 16, pp. 57-66 (1995).

Folkman, J., "Angiogenesis in cancer, vascular rheumatoid and other disease", Nature Medicine, vol. 1, No. 1, pp. 27-31 (1995).

Haque, S.A. et al., "Monastrol, a Prototype Anti-Cancer Drug That Inhibits a Mitotic Kinesin, Induces Rapid Bursts of Axonal Outgrowth From Cultured Postmitotic Neurons", Cell Motility and the Cytoskeleton, vol. 58, pp. 10-16 (2004).

Henry, J.R. et al., "p38 mitogen-activated protein kinase as a target for drug discovery", Drugs of the Future, vol. 24, No. 12, pp. 1345-1354 (1999).

Jaffari, G.A. et al., "Some Oxidation Reactions of Monochloramine", J. Chem. Soc. (C), pp. 823-826 (1971).

Jakeman, L.B. et al., "Development Expression of Binding Sites and Messenger Ribonucleic Acid for Vascular Endothelial Growth Factor Suggests a Role for This Protein in Vasculogenesis and Angiogenesis", Endocrinology, vol. 133, No. 2, pp. 848-859 (1993).

Kapoor, T.M. et al., "Probing Spindle Assembly Mechanisms with Monastrol, a Small Molecule Inhibitor of the Mitotic Kinesin, Eg5", The Journal of Cell Biology, vol. 150, No. 5, pp. 975-988 (2000).

Kolch, W. et al., "Regulation of the expression of the VEGF/VPS and its receptors: role in tumor angiogenesis", Breast Cancer Research and Treatment, vol. 36, pp. 139-155 (1995).

Mayer, T.U. et al., "Small Molecule Inhibitor of Mitotic Spindle Bipolarity Identified in a Phenotype-Based Screen", Science, vol. 286, pp. 971-974 (1999).

Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).

Moreland, L.W. et al., "Etanercept Therapy in Rheumatoid Arthritis: A Randomized, Controlled Trial", Ann. Intern. Med., vol. 130, No. 6, pp. 478-486 (1999).

Neunhoeffer, H. et al., "Cycloaddition Reactions with Methoxy- and Dialkylamino-1,2,4-triazines", Liebigs Ann. Chem., pp. 1413-1420 (1977).

Otter, B.A. et al., "Conformational Properties of Purine-Like C-Nucleosides", Nucleosides & Nucleotides, vol. 15, Nos. 1-3, pp. 793-807 (1996).

Patil, S.A. et al., "Synthesis of Pyrrolo[2,1-f][1.2.4]triazine Congeners of Nucleic Acid Purines via the V-Amination of 2-Substituted Pyrroles", J. Heterocyclic Chem., vol. 31, pp. 781-786 (1994).

Quintela, J.M. et al., "A Ready One-pot Preparation for Pyrrolo[2,1-f][1,2,4]triazine and Pyrazolo[5,1-c]pyrimido[4,5-e][1,2,4]triazine Derivatives", Tetrahedron, vol. 52, no. 8, pp. 3037-3048 (1996).

Raingeaud, J. et al., "MKK3- and MKK6-Regulated Gene Expression is Mediated by the p38 Mitogen-Activated Protein Kinase Signal Transduction Pathway", Molecular and Cellular Biology, vol. 16, No. 3, pp. 1247-1255 (1996).

Rankin, E.C.C. et al., "The Therapeutic Effects of an Engineered Human AntiTumor Necrosis Factor Alpha Antibody (CDP571) in Rheumatoid Arthritis", British Journal of Rheumatology, vol. 34, pp. 334-342 (1995).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Selic, L. et al., "Transformations of Alkyl 2-(2,2-Disubstituted-ethenyl)amino-3-dimethylaminoprop-2-enoates: Synthesis of Alkyl 3,4-Disubstituted- and Alkyl 1-Acyl-3, 4-disubstituted Pyrrole-2-carboxylates", Synthesis, No. 3, pp. 479-482 (1999).

Senger, D.R. et al., "Vascular permeability factor (VPF, VEGF) in tumor biology", Cancer and Metastasis Reviews, vol. 12, pp. 303-324 (1993).

Shen, Y, et al., "Comparison of Electrophilic Amination Reagents for N-Amination of 2-Oxazolidinones and Application to Synthesis of Chiral Hydrazones", J. Org. Chem., vol. 67, No. 17, pp. 6236-6239 (2002).

Simone, J.V., Part XIV: Oncology, No. 154: "Introduction", Cecil Textbook of Medicine, 20th Ed., W.B. Saunders Company, publ., Bennett, J.C. et al., eds., pp. 1004-1008 (1996).

Skobe, M. et al., "Halting angiogenesis suppresses carcinoma cell invasion", Nature Medicine, vol. 3, No. 11, pp. 1222-1227 (1997).

Suzuki, M. et al., "A Convenient Synthesis of 3-Substituted Pyrrole-2,4-dicarboxylic Acid Esters", J. Org. Chem., vol. 39, No. 13, p. 1980 (1974).

Svete, J. et al., "2-Benzoyl-2-ethoxycarbonylvinyl-1 and 2-Benzoylamino-2-methoxycarbonylvinyl-1 as N-Protecting Groups in Peptide Synthesis. Their Application in the Synthesis of Dehydropeptide Derivatives Containing N-Terminal 3-Heteroarylamino-2,3-dehydroalanine", J. Heterocyclic Chem., vol. 34, pp. 177-193 (1997).

Taft, W.E. et al., "as-Triazines. I. 5-Sulfanilamido Derivatives and Intermediates", J. Med. Chem., pp. 883-887 (1967).

Terman, B.I. et al., "Identification of the KDR Tyrosine Kinase as a Receptor for Vascular Endothelial Cell Growth Factor", Biochemical and Biophysical Research Communications, vol. 187, No. 3, pp. 1579-1586 (1992).

Toplak, R. et al., "Ethyl 2-(2-Acetyl-2-ethoxycarbonyl-1-ethenyl)amino-3-dimethylaminopropenoate in the Synthesis of Heterocyclic Systems. The Synthesis of Substituted 3-Aminoazolo- and -Azinopyrimidinones, Pyridopyridinones and Pyranones", Heterocycles, vol. 50, No. 2, pp. 853-866 (1999).

West, A.R., Basic Solid State Chemistry, John Wiley & Sons Ltd., publ., pp. 356-365 (1988).

Wolf, M.E., ed., Burger's Medicinal Chemistry and Drug Discovery, 5th Ed., vol. I: Principles and Practice, John Wiley & Sons, Inc., publ., pp. 975-977 (1995).

\* cited by examiner

PROCESS FOR PREPARING PYRROLOTRIAZINE ANILINE COMPOUNDS USEFUL AS KINASE INHIBITORS

This application claims a benefit of priority from U.S. Provisional Application No. 60/600,935, filed Aug. 12, 2004, the entire disclosure of which is herein incorporated by reference.

FIELD OF THE INVENTION

The present invention relates to a process for preparing a pyrrolotriazine aniline compound, such as 4-[[5-[(cyclopropylamino)carbonyl]-2-methylphenyl]amino]-5-methyl-N-propylpyrrolo[2,1-f][1,2,4]triazine-6-carboxamide, which is a p38 kinase inhibitor and is useful in treating p38 kinase related diseases such as rheumatoid arthritis.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others (Henry et al., *Drugs Fut.*, 24:1345–1354 (1999); Salituro et al., *Curr. Med. Chem.*, 6:807–823 (1999)). Evidence in human patients indicates that protein antagonists of cytokines are effective in treating chronic inflammatory diseases, such as, for example, monoclonal antibody to TNF-α (Enbrel) (Rankin et al., *Br. J. Rheumatol.*, 34:334–342 (1995)), and soluble TNF-α receptor-Fc fusion protein (Etanercept) (Moreland et al., *Ann. Intern. Med.*, 130:478–486 (1999)).

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to SmithKline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

U.S. application Ser. No. 10/420,399 filed Apr. 22, 2003 (hereinafter the Ser. No. 10/420,399 application) discloses compounds which are inhibitors of p38 kinase, which may be used for treating p38 kinase associated conditions including rheumatoid arthritis, and which compounds have the formula (I)

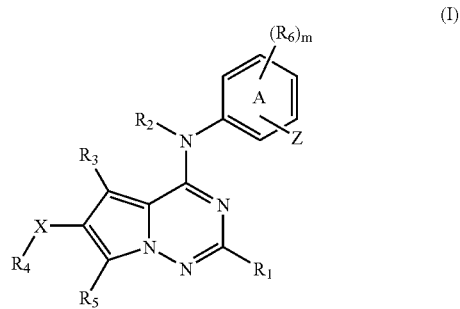

enantiomers, diastereomers, salts, and solvates thereof, wherein

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Z is —C(=O)NR$_{10}$—B$^b$, —(CH$_2$)—C(=O)NR$_{10}$—B$^c$, —NR$_{10a}$C(=O)—B$^a$, —(CH$_2$)—NR$_{10a}$C(=O)—B$^c$, —NR$_{10a}$C(=O)NR$_{10}$—B, —NR$_{10}$SO$_2$—B, —SO$_2$NR$_{10}$—B, —C(=O)B$^a$, —CO$_2$—B$^e$, —OC(=O)—B$^a$, —C(=O)NR$^{10}$—NR$_{10a}$—B$^d$—NR$_{10}$CO$_2$—B$^a$ or —C(=O)NR$_{10}$—(CH$_2$)C(=O)B$^a$;

B is
(a) optionally-substituted cycloalkyl, optionally-substituted heterocyclo, or optionally substituted heteroaryl; or
(b) aryl substituted with one R$_{11}$ and zero to two R$_{12}$;

B$^a$ is optionally substituted alkyl, optionally-substituted cycloalkyl, optionally-substituted heterocyclo, optionally substituted aryl, or optionally substituted heteroaryl;

B$^b$ is
(a) optionally-substituted cycloalkyl, optionally-substituted heterocyclo, or optionally substituted heteroaryl;
(b) aryl substituted with one R$_{11}$ and zero to two R$_{12}$; or
(c) —C(=O)R$_{13}$, —CO$_2$R$_{13}$, —C(=O)NR$_{13}$R$_{13a}$;

B$^c$ is optionally substituted alkyl, optionally substituted alkoxy, optionally-substituted cycloalkyl, optionally-substituted heterocyclo, optionally substituted aryl, or optionally substituted heteroaryl;

B$^d$ is hydrogen, —C(=O)R$_{13}$, or —CO$_2$R$_{13}$;

B$^e$ is hydrogen, optionally substituted alkyl, optionally-substituted cycloalkyl, optionally-substituted heterocyclo, optionally substituted aryl, or optionally substituted heteroaryl;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C(=O)R$_{14a}$, —NR$_{14}$CO$_2$R$_{14a}$, —NR$_{14}$C(=O)NR$_{14a}$R$_{14b}$, halogen, nitro, and cyano;

$R_2$ is hydrogen or $C_{1-4}$alkyl;

$R_3$ is hydrogen, methyl, perfluoromethyl, methoxy, halogen, cyano, $NH_2$, or $NH(CH_3)$;

$R_4$ is selected from:
- (a) hydrogen, provided that $R_4$ is not hydrogen if X is —S(=O)—, —SO$_2$—, —NR$_8$CO$_2$—, or —NR$_8$SO$_2$—;
- (b) alkyl, alkenyl, and alkynyl optionally independently substituted with keto and/or one to four $R_{17}$;
- (c) aryl and heteroaryl either of which may be optionally independently substituted with one to three $R_{16}$; and
- (d) heterocyclo and cycloalkyl either of which may be optionally independently substituted with keto and/or one to three $R_{16}$; or
- (e) $R_4$ is absent if X is halogen, nitro, or cyano;

$R_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy, wherein each $R_6$ group in turn may be further substituted by one to two $R_{18}$;

$R_8$ and $R_9$ are independently selected from hydrogen, alkyl, substituted alkyl, aryl, cycloalkyl, heterocyclo, and heteroaryl;

$R_{10}$ and $R_{10a}$ are independently selected from hydrogen, alkyl, substituted alkyl, alkoxy, and aryl;

$R_{11}$ is selected from
- (a) alkyl, haloalkyl, alkoxy, haloalkoxy, —SO$_2$alkyl, cycloalkyl, heterocyclo, and heteroaryl any of which may be optionally substituted; or
- (b) halo, cyano, amino, alkylamino, and dialkylamino;

$R_{12}$ is selected from alkyl, $R_{17}$, and $C_{1-4}$alkyl substituted with keto (=O) and/or one to three $R_{17}$;

$R_{13}$ and $R_{13a}$ are independently selected from hydrogen, optionally substituted alkyl, optionally substituted cycloalkyl and optionally substituted aryl;

$R_{14}$, $R_{14a}$ and $R_{14b}$ are independently selected from hydrogen, alkyl, substituted alkyl, aryl, cycloalkyl, heterocyclo, and heteroaryl, except when $R_{14}$ is joined to a sulphonyl group as in —S(=O)$R_{14}$, —SO$_2R_{14}$, and —NR$_{14a}$SO$_2R_{14}$, then $R_{14}$ is not hydrogen;

$R_{16}$ is selected from alkyl, $R_{17}$, and $C_{1-4}$alkyl substituted with keto (=O) and/or one to three $R_{17}$;

$R_{17}$ is selected from
- (a) halogen, haloalkyl, haloalkoxy, nitro, cyano, —SR$_{23}$, —OR$_{23}$, —NR$_{23}R_{24}$, —NR$_{23}$SO$_2R_{25}$, —SO$_2R_{25}$, —SO$_2$NR$_{23}R_{24}$, —CO$_2R_{23}$, —C(=O)$R_{23}$, —C(=O)NR$_{23}R_{24}$, —OC(=O)$R_{23}$, —OC(=O)NR$_{23}R_{24}$, —NR$_{23}$C(=O)$R_{24}$, —NR$_{23}$CO$_2R_{24}$;
- (b) aryl or heteroaryl either of which may be optionally substituted with one to three $R_{26}$; or
- (c) cycloalkyl or heterocyclo optionally substituted with keto(=O) and/or one to three $R_{26}$;

$R_{18}$ and $R_{26}$ are independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, $C_{1-4}$alkylthio, aryl, heterocyclo, (aryl)alkyl, aryloxy, and (aryl)alkoxy;

$R_{23}$ and $R_{24}$ are each independently selected from hydrogen, alkyl, alkenyl, substituted alkyl, substituted alkenyl, aryl, cycloalkyl, heteroaryl, and heterocyclo;

$R_{25}$ is selected from alkyl, substituted alkyl, aryl, heteroaryl, cycloalkyl and heterocyclo; and m is 0, 1, 2 or 3.

The 10/420,399 application further discloses that the compounds of formula (I) may be prepared using the following reaction sequences.

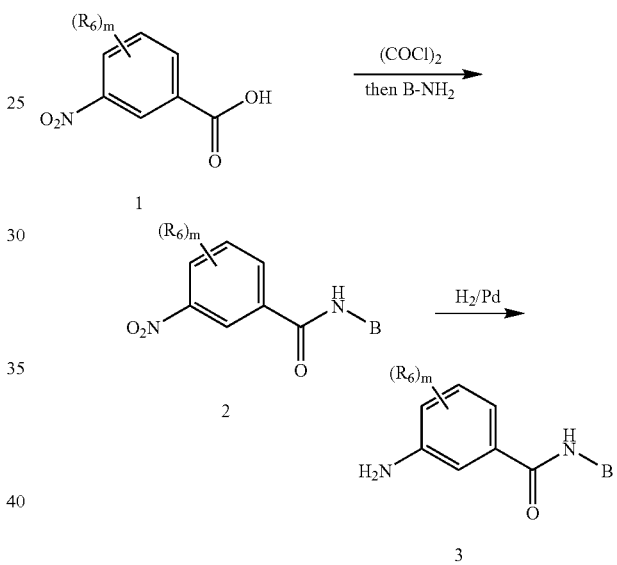

SCHEME 1

Scheme 1 is described as follows.

"Commercially-available compound (1) can be reacted with oxalyl chloride with heating and then concentrated in vacuo and reacted with an amine B—NH$_2$ in the presence of a base, such as diisopropylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 2 to produce compounds (8) of Scheme 2."

SCHEME 2

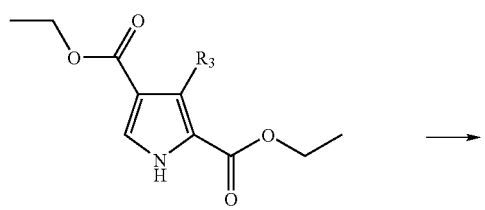

4a

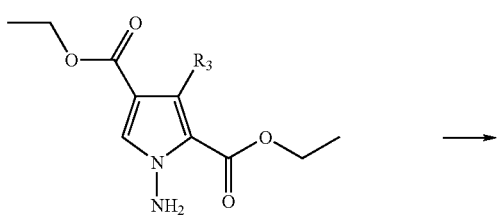

4

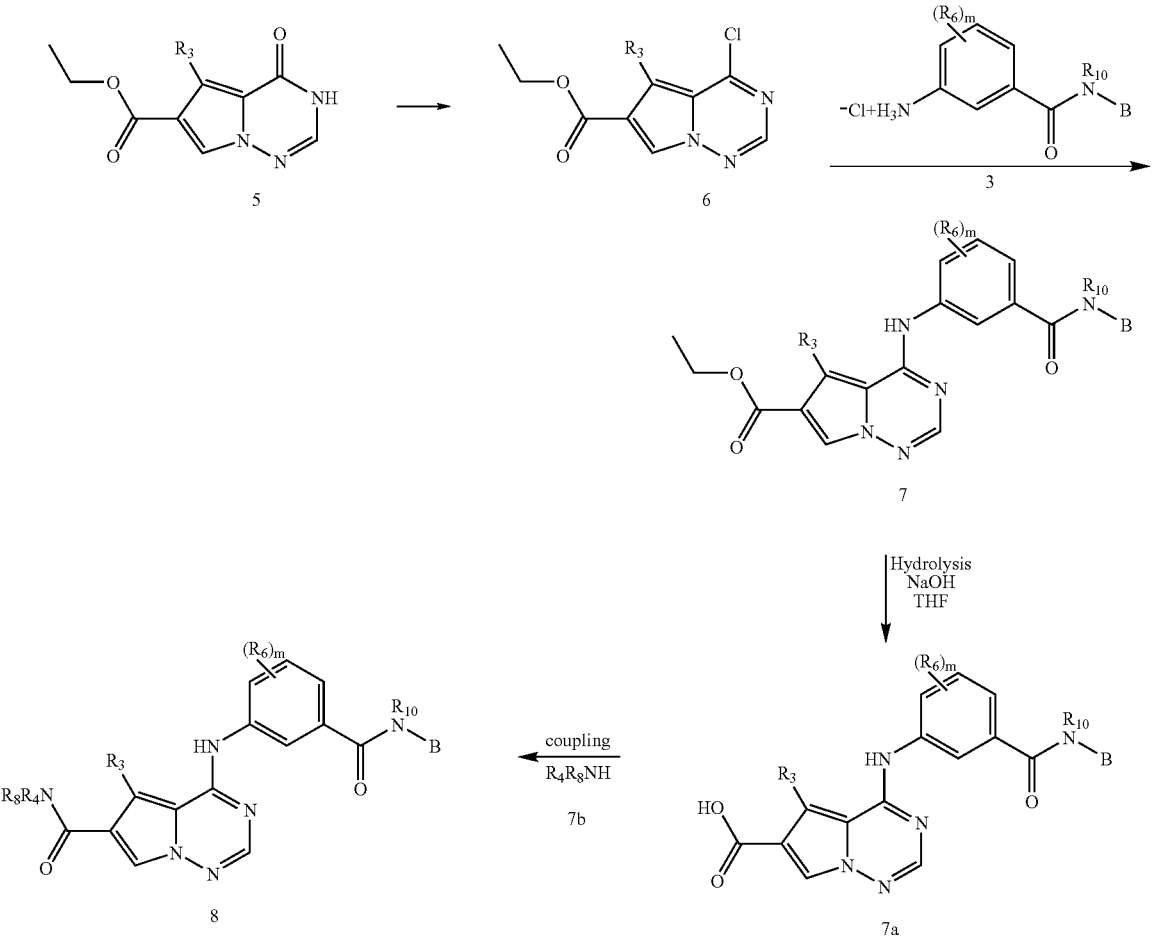

Referring to Scheme 2, 3-methyl-1-pyrrole-2,4-diethyl ester can be reacted with chloramine in ether to produce compound (4). Reacting compound (4) in formamide with acetic acid produces compound (5). Compound (5) can be reacted with DIPEA and $POCl_3$ in toluene to produce compound (6). Compound (6) can be reacted with DIPEA and compound (3) in DMF to produce compound (7). Compound (7) is hydrolyzed in THF with NaOH to produce acid intermediate (7a) which upon treatment with HOBt, EDCI and the appropriate amine (7b) in DMF produces compound (8).

Included among the many compounds covered by the Ser. No. 10/420,399 application is the compound of the structure

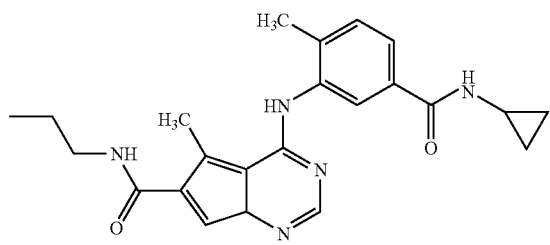

also referred to as 4-[[5-[(cyclopropylamino)carbonyl]-2-methylphenyl]amino]-5-methyl-N-propylpyrrolo[2,1-f][1,2,4]triazine-6-carboxamide or the free base thereof.

As can be seen from the above Reaction Scheme 2, the ester 7 is converted to the amide 8 employing a two step process wherein ester 7 is hydrolyzed to the corresponding acid 7a which is made to undergo a coupling reaction with the amine 7b to produce the amide 8.

Although the above two step procedure for producing amide 8 from ester 7 is adequate, any improvement in such two step procedure which involved direct conversion of ester 7 to amide 8 (without the hydrolysis step) would be a most welcome improvement.

BRIEF DESCRIPTION OF THE INVENTION

In accordance with the present invention, a process is provided for preparing a pyrrolotriazine aniline amide compound II which has the structure (amide compound II)

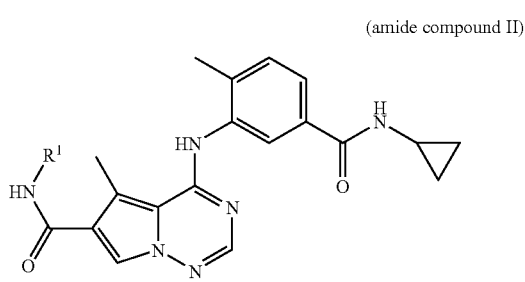

where $R^1$ is lower alkyl or aryl, which process includes the steps of a. providing a mixture of a strong organometallic base such as an alkyl lithium compound, for example, hexyllithium or n-butyllithium, and an amine of the structure $R^1NH_2$ (III) where $R^1$ is lower alkyl or aryl, in an organic solvent, such as tetrahydrofuran;

b. providing an ester of the structure I

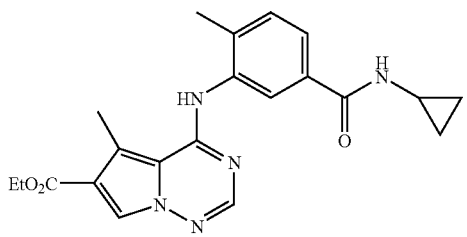
(ester compound I)

preferably in the form of a suspension in an organic solvent (which is preferably the same as the organic solvent employed in step a); and c. reacting the mixture in step a. and ester I in step b. to form the amide product II.

The above reaction will be carried out at a temperature within the range from about −10° C. to about 110° C., preferably from about −5° C. to about 95° C.

The process of the invention provides an effective one-step direct aminolysis procedure for preparing the amide product II.

In a preferred embodiment of the process of the invention, the strong organometallic base will be an alkyllithium compound, preferably hexyllithium or n-buthyllithium, the organic solvent for each of the mixture of the strong organometallic base and the amine III, and the suspension of the ester compound I is tetrahydrofuran, the amine C is propylamine, and the reaction is carried out at a temperature within the range from about −10° to about 30° C., preferably from about −5 to about 25° C.

In another preferred embodiment of the process of the invention, the organometallic base employed is n-butyllithium and the above reaction is carried out at a temperature with the range from about 10° to about 40° C., preferably from about 20° to about 30° C.

In still another preferred embodiment of the process of the invention, the organometallic base employed is n-butyllithium, the amine III employed is n-propylamine in 2,2,2-trifluoroethanol and the reaction is carried out at a temperature within the range from about 50° to about 120° C., preferably for about 85° to about 95° C.

In another preferred embodiment of the process of the invention, trimethylaluminum in hexanes is employed, the amine employed is n-propylamine in methylene chloride and the reaction is carried out at a temperature within the range from about 40° to about 80° C., preferably from about 50° to about 70° C.

DETAILED DESCRIPTION OF THE INVENTION

Unless otherwise indicated, the term alkyl or "lower" alkyl, as used herein, denotes branched or unbranched hydrocarbon chains, preferably having about 1 to about 8 carbons, such as, methyl, ethyl, n-propyl, iso-propyl, n-butyl, sec-butyl, isobutyl, tert-butyl, 2-methylpentyl pentyl, hexyl, isohexyl, heptyl, 4,4-dimethyl pentyl, octyl, 2,2,4-trimethylpentyl and the like, which lower alkyl group may be optionally substituted with one, two, three or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings), for example

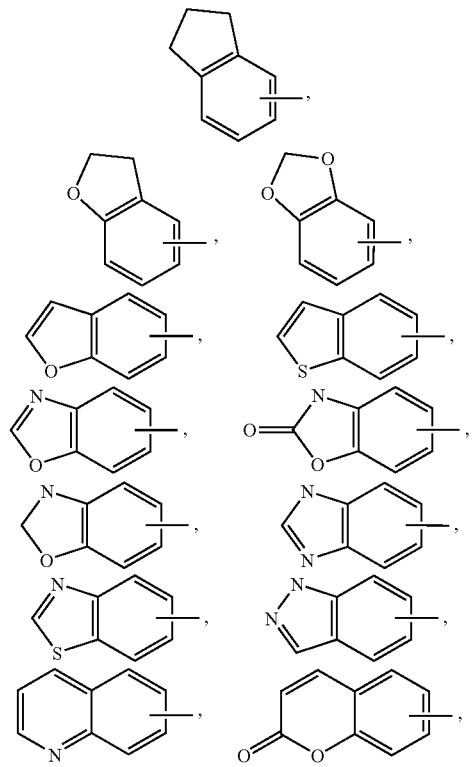

The aryl group may be optionally substituted with one, two, three or more functional groups, such as halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, adamantyl,

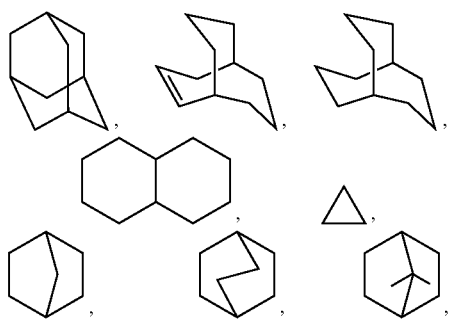

any of which groups may be optionally substituted with 1 to 4 substituents such as halogen, alkyl, alkoxy, hydroxy, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as:

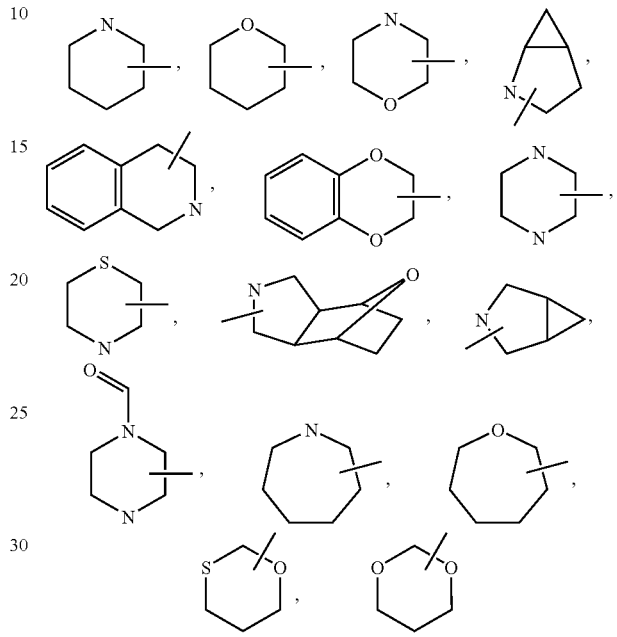

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

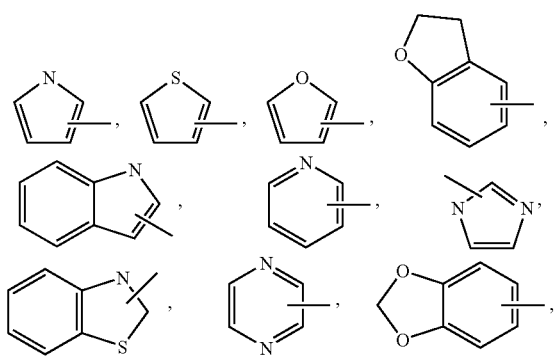

-continued

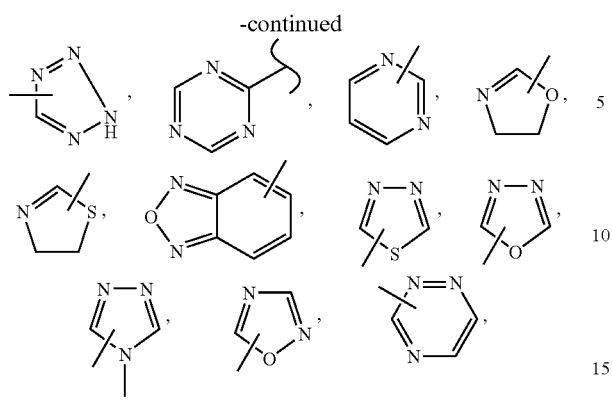

and the like.

The term "cycloheteroalkylalkyl" as used herein alone or as part of another group refers to cycloheteroalkyl groups as defined above linked through a C atom or heteroatom to a —(CH$_2$)$_r$— chain.

The term "heteroarylalkyl" or "heteroarylalkenyl" as used herein alone or as part of another group refers to a heteroaryl group as defined above linked through a C atom or heteroatom to a —(CH$_2$)$_r$— chain, alkylene or alkenylene as defined above.

In carrying out the process of the invention, the strong organometallic base will be employed in a molar ratio to the ester compound I within the range from about 3:1 to about 6.5:1, preferably from about 5.0:1 to about 6.2:1, and the amine III will be employed in a molar ratio to ester compound I within the range from about 4:1 to about 7.3:1, preferably from about 5.5:1 to about 7:1. The ratio of amine III to the organometallic base will be in the range of 1.1 to 1.2.

The strong organometallic base will preferably be an alkyllithium base, such as hexyllithium or n-butyllithium although other strong organometallic bases may be employed such as lithium hexamethyldisilazane, lithium diisopropyl amide, sodium diisopropylamide, or potassium diisopropylamide. Furthermore, trimethylaluminium can also be employed as an organometallic base.

Organic solvents which may be employed in forming a mixture of the strong organometallic base and amine III include, but are not limited to, tetrahydrofuran, methylene chloride, 2,2,2-trifluoroethanol, and hexanes with tetrahydrofuran being preferred.

Similar organic solvents as set above may be employed in forming a suspension of the ester compound I, although the ester compound may be employed without a solvent. It is preferred that the ester compound I be employed as a suspension in an organic solvent which is the same solvent employed for the strong organometallic base.

The starting ester compound I may be prepared in accordance with the following reaction sequence:

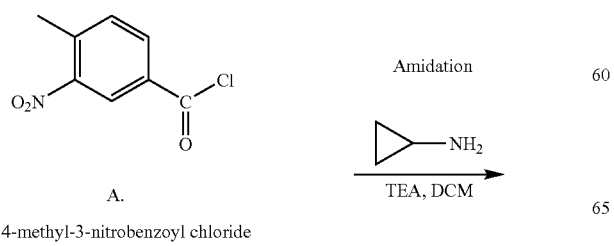

A.
4-methyl-3-nitrobenzoyl chloride

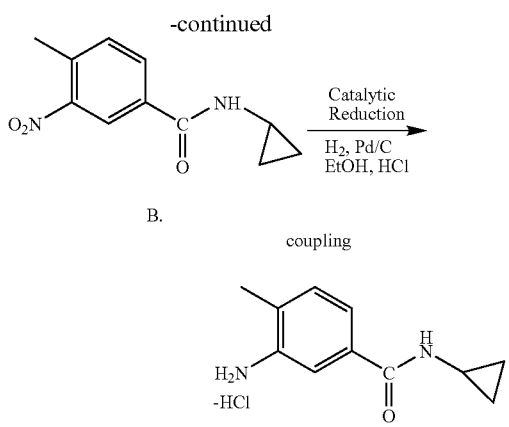

The intermediate C is prepared by the amidation of 4-methyl-3-nitrobenzoyl chloride (A) with cyclopropylamine followed by catalytic reduction and hydrogen chloride salt formation to obtain the intermediate C.

The preparation of intermediate E starts with conversion of pyrrole E$^1$

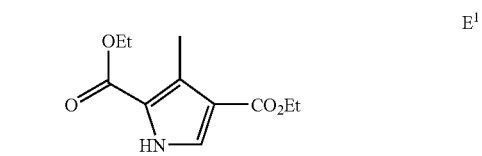

to the 1-amino pyrrole $E^2$

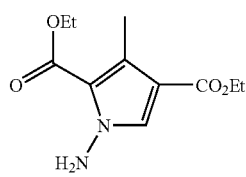

and is followed by condensation of $E^2$ with formamide and acid catalyzed cyclization yielding intermediate D. Chlorination of D yields the intermediate E.

Coupling intermediate C with intermediate E yields ester intermediate I.

A full disclosure of the above process is disclosed in U.S. application Ser. No. 10/420,399 filed Apr. 22, 2003 which is incorporated herein by reference.

UTILITY

The amide compound of formula II is a selective inhibitor of p38 kinase activity, and in particular, isoforms p38α and p38β. Accordingly, amide II has utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of its activity as an inhibitor of p-38α/β kinase, amide compound II is useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the amide compound II includes, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, the amide compound II p38 inhibitor inhibits the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The amide II also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The methods of treating p38 kinase-associated conditions may comprise administering amide II alone or in combination with each other and/or other suitable agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDS) such as ibuprofen, celecoxib and rofecoxib; steroids such as prednisone or dexamethasone; antiviral agents such as abacavir; antiproliferative agents such as methotrexate, lefluonomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the amide II, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The amide II may be incorporated in pharmaceutical compositions capable of treating p38-kinase associated conditions, including TNF-α, IL-1, and/or IL-8 mediated conditions, as described above. The compositions may optionally contain other therapeutic agents as described above, and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The amide II may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of amide II may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

The amides II have been tested in one or more of the assays described below and have shown activity as inhibitors of p38α/β enzymes and TNF-α.

BIOLOGICAL ASSAYS

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.,* 1247–1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.).

Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; [γ-$^{33}$P]ATP, 3 nM; MBP (Sigma, #M1891), 2 μg/well; p38, 10 nM; and DMSO, 0.3%.

TNF-α Production by LPS-Stimulated Mice

Mice (Balb/c female, 6–8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2:O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

ABBREVIATIONS

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
Pd=palladium
Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt=room temperature
ret. t.=HPLC retention time (minutes)
AP=HPLC area percent
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point

EXAMPLES

In the Example 1, designations associated with HPLC data reflect the following conditions:
 a. Column: YMC ODSA S-5 5 u C18 4.6×50 mm; Solvent: solvent A=10% MeOH/90% water/0.1% TFA, and solvent B=90% MeOH/10% water/0.1% TFA; Method: 4 min gradient;
 b. Column: YMC S-5 ODS 4.6×50 mm; Solvent: solvent A=10% MeOH/90% water/0.2% $H_3PO_4$, and solvent B=90% MeOH/10% water/0.2% $H_3PO_4$; Method: 4 min gradient.

In the Examples 2 and 3, designations associated with HPLC data reflect the following conditions:
 Column: YMC Hydrosphere C18 4.6×150 mm, 3 u; Solvent: solvent A=0.05% TFA/water, and solvent B=0.05% TFA/MeCN Method: 10–35% B over 30 min, 35–70% B over 15 min. Flow rate 1 ml/min, 250 nm.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

Example 1

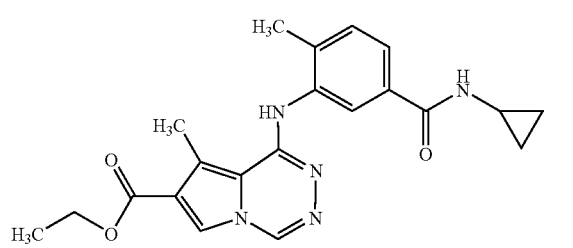
(Ester I)

Step 1:

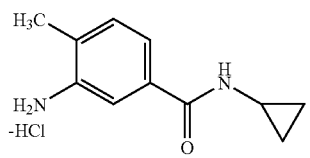
(1)

To a cold solution of triethylamine (3.74 kg, 37.0 mol) in dichloromethane (130.6 kg) was added cyclopropylamine (2.38 kg, 41.7 mol). The mixture was stirred at −5 to 0° C. for 20 min. The solution of 4-methyl-3-nitrobenzoyl chloride (6.8 kg, 34.1 mol) in dichloromethane (14.6 kg) was added at such a rate to maintain the temperature<5° C. The mixture was stirred at 0 to 5° C. until its completion by HPLC analysis. The reaction was quenched with 1N HCl solution (49.6 L) (T<15° C.), and the mixture was allowed to warm up to rt. The organic layer was separated. The aqueous layer was extracted with dichloromethane (26.2 kg). The combined organic layers were washed with 5% $NaHCO_3$ (49.6 L) and brine (33.0 L). The solvent was exchanged from dichloromethane to ethanol by distillation. The final ethanol solution volume was ~98.6 L. To this solution was charged 5% Pd/C (0.34 kg). The mixture was hydrogenated under 40 psi. The reaction temperature was in the range of 35 to 45° C. The cooling was applied if necessary. Once the reaction went to completion, the catalyst was filtered off. The filtrate was concentrated to a volume ~68.0 L. The solution was cooled to 0 to 5° C., followed by addition of 12N HCl (~2.7 L). The resulting slurry was stirred for 1 h. The slurry was filtered, and the cake was washed with cold ethanol (10.9 kg). The cake was dried under vacuum at 40–50° C. for 20 h to afford 6.8 kg of compound 1 (yield: 88.3%) as an off-white solid.

Step 2:

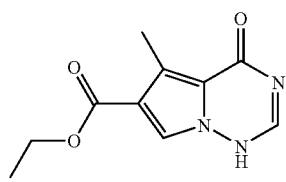

Part a.

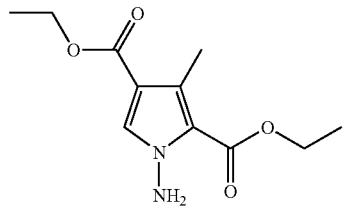

To a solution of the 3-methyl-1-pyrrole-2,4-diethyl ester (100 mg) (J. *Heterocyclic Chem* Vol. 34 (1997), at pp. 177–193; *Heterocycles*, Vol. 50 (1999), at pp. 853–866; *Synthesis* (1999), at pp. 479–482), generally, the synthesis of pyrroles is described by the procedure of M. Suzuki, M. Miyoshi, and K. Matsumoto *J. Org. Chem.* 1974, 39 (1980)) in DMF (0.44M)) was added either NaH or KOtBu (1.2 equiv) at rt. This solution was stirred for 30–45 minutes. Chloramine in ether (ca. 0.15M, 1 eq.) was added via syringe. The solution was stirred for 1.5 h or until starting material was converted to product as judged by HPLC analysis. The reaction was then quenched with aq. $Na_2S_2O_3$ and extracted with EtOAc or $Et_2O$. The organic extracts were washed with water and brine and then dried over sodium sulfate. Title compound a. was obtained in >90% yield. $NH_2Cl$ in ether was prepared according to the procedure of Nunn, *J. Chem. Soc.* (C), (1971) at p. 823.

Part b.

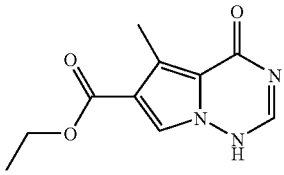

To a solution of Part a. compound a. (2 g) in formamide (8 mL) was added acetic acid (20% by weight), and the mixture was heated at 120° C. for 24 h. The reaction mixture was cooled and water added (32 mL) to precipitate the product. The solids were collected by filtration and washed with EtOAc to furnish title compound b. as a yellow solid (90%).

Step 3:

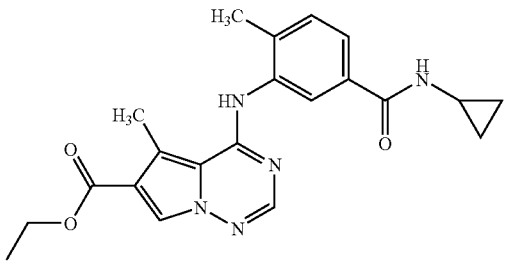

Part a.

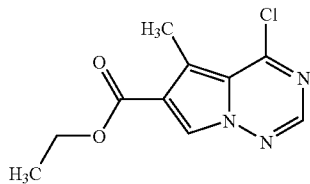

To a suspension of step 2 compound b oxopyrrolotriazine (750 g, 3.4 mmol) in toluene (11.36 kg) was added phosphorus oxychloride (643 g, 4.2 mol) and N,N-DIPEA (484 g, 3.7 mol). The resulting mixture was heated to 108–112° C. for 17–19 h. Oxopyrrolotriazine was <2% by HPLC analysis at this point. The mixture was allowed to cool to 0° C., and then the aqueous $K_2HPO_4$ (~17%, 13.5 kg) was added slowly (T<5° C.). The organic layer was separated and washed with the aqueous $K_2HPO_4$ (~17%, 2.6 kg) and water (1.7 kg). The organic layer was filtered through a bed of celite, and the filtrate was concentrated in vacuo to a volume (~7 L). DMF (4 L) was added. Evoparation all the toluene gave a solution of the title compound a in DMF.

Part b.

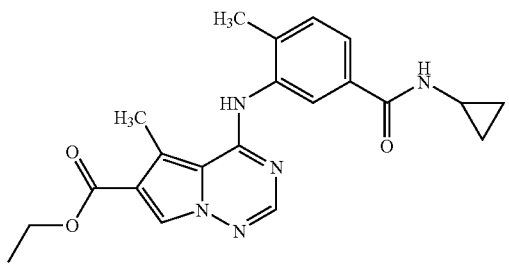

To a 20 L reactor was charged step 1 compound 1 (777 g, 3.4 mol), followed by addition of diisopropylethylamine (418 g, 3.2 mol) and DMF (2.4 kg). The solution from step 3 compound a and DMF (3.0 kg) were added. The mixture was heated to 45° C. and stirred at 45° C. until completion (~1 h). The mixture was cooled to 35° C., and the aqueous solution of $K_2HPO_4$ (18.5%, 3.3 kg) was added over a 2 h period. The resulting slurry was stirred at RT for overnight. The solid was filtered, and the cake was washed with water (7.6 L), acetonitrile (1.8 kg) and toluene (3.3 kg). The solid was dried under vacuum at 40° C. to afford Example 1 ester (1.2 kg, 87% yield) as an off-white solid. HPLC Ret. T.=3.19 min.; LC/MS $(M+H)^+=394.31$.

Example 1A

Two Step Aminolysis

Amide

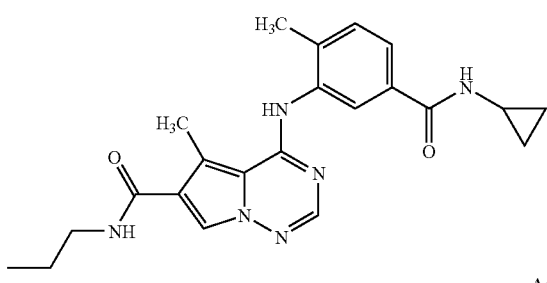

Acid

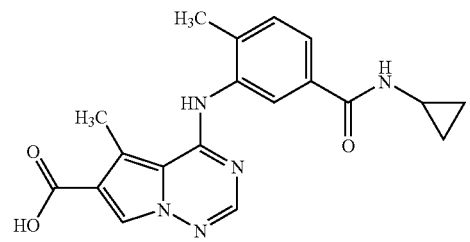

Part a.

A solution of Example 1 (0.86 g, 2.20 mmol, 1.0 eq.) in THF (4.0 mL) and 1 N aqueous NaOH (9.0 mL, 4.1 eq.) was stirred at 60° C. overnight. After cooling to RT, the reaction mixture was concentrated in vacuo but not to dryness. To the solution at 0° C. was added 1 N aqueous hydrochloric acid until it was acidic and the precipitate was collected and dried to afford crude Example 1A acid (0.51 g, 64.0% yield). HPLC Ret. t.=2.400 min.; LC/MS $(M+H)^+=366.06^+$. The filtrate was then extracted with EtOAc (3×) and the organic layers were combined, dried over sodium sulfate, and concentrated in vacuo to give Example 1A acid (0.035 g, 4.4% yield).

Part b.

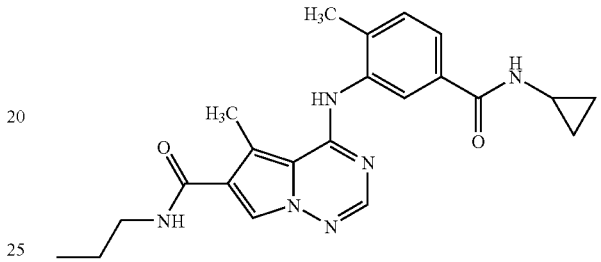

A solution of Part a. acid (0.026 g, 0.071 mmol, 1.0 eq.), EDC (0.021 g, 0.11 mmol, 1.5 eq.), HOBt (0.015 g, 0.11 mmol, 1.5 eq), n-propylamine (0.015 mL, 0.15 mmol, 2.1 eq.) and DIPEA (0.040 mL, 0.23 mmol, 3.2 eq.) in DMF (0.20 mL) was shaken at RT overnight. Water (1 mL) was added and the precipitate collected by filtration, washed with water, and dried to give Example 1A amide (0.021 g, 70% yield); HPLC Ret. t.=2.883 min.; LC/MS $(M+H)^+=421.18^+$.

Example 2

Direct Aminolysis Procedure

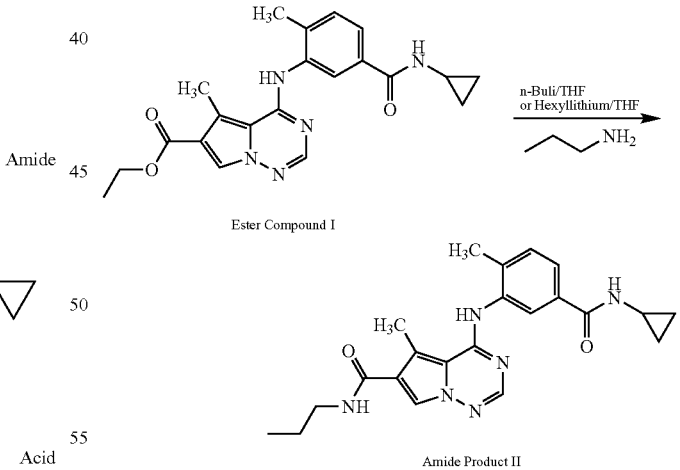

1. Aminolysis with Hexyllithium

To a dried 100 ml flask was added THF (10 ml) under nitrogen, which was then cooled to −10° C. Hexyllithium (2.3 M in hexane, 6.5 ml, 15.0 mmol) was added slowly (exothermic, temperature was up to 5° C.), followed by dropwise addition of propylamine (1.01 g, 1.4 ml, 17.1 mmol) at such a rate to maintain the temperature below 5° C. The resulting mixture was stirred at 0° C. for 20 minutes. A suspension of ester compound I (1.0 g, 2.5 mmol) in THF (12 ml) was added over a 10 minute period (exothermic, T<5° C.). After being stirred at 0° C. for 20 minutes, the mixture was allowed to warm to room temperature and stirred for 5 hours. Ester compound I was <0.1 AP at this point by HPLC analysis. The mixture was cooled to −5° C. Acetic acid (2 ml) was added slowly to maintain the temperature<10° C. The resulting thick slurry was stirred at room temperature for 20 minutes, and then solvents were exchanged with DMF (15 ml) on a rotavapor. To the resulting yellow slurry, water (15 ml) was added slowly to keep T<25° C. During the addition of water, the slurry became a clear solution, and a new slurry was formed. The slurry was stirred at room temperature for overnight. In the morning the slurry was filtered and the solid was washed with DMF/water (1:1, 5 ml), water (5 ml) and acetone (5 ml). The cake was dried under vacuum at 55° C. for 24 hours to afford 0.90 g of amide product II (yield: 87.2%) as a white solid.

HPLC: 99.70 AP.

2. Aminolysis with n-butyllithium

To a dried 100 ml of flask was added THF (10 ml) under nitrogen and then cooled to −10° C. n-Butyllithium (2.5 M in hexane, 6.0 ml, 15.0 mmol) was added slowly, followed by dropwise addition of propylamine (0.98 g, 16.5 mmol) at such a rate to keep the temperature below 0° C. The resulting mixture was stirred at 0° C. for 20 minutes. A suspension of ester compound I (1.0 g, 2.5 mmol) in THF (12 ml) was added over a 10 minute period (T<5° C.). After being stirred at 0° C. for 30 minutes, the mixture was allowed to warm to room temperature and stirred for overnight (~22 h, Note 1). Compound I was not detected at this point by HPLC analysis. The mixture was cooled to −7° C. Acetic acid (2 ml) was added dropwise to maintain the temperature<10° C. The resulting thick slurry was stirred at 5° C. for 2 hours and at room temperature for 20 minutes, followed by evaporation on a rotavapor to give a wet yellow solid. To this solid was added acetone (10 ml) and water (20 ml). The slurry was stirred at room temperature for one and half hours. Filtration gave a white solid. This solid was washed with 35% acetone in water (10 ml), water (5 ml) and acetone (5 ml). The cake was dried under vacuum at 55° C. for the weekend to afford 0.94 g of amide product II (yield: 91.0%) as a white solid. HPLC: 99.76 AP. Note 1: Compound I was ~0.056 AP at 2.5 hours.

Example 3

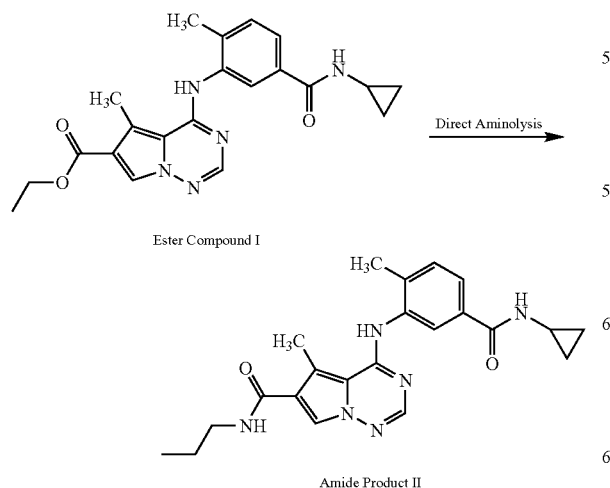

Ester Compound I

Direct Aminolysis

Amide Product II

Method A:

A solution of n-propylamine (6.5 eq) in THF (20 ml/g of ester compound I) was cooled to ~−5° C. and was slowly treated with 2.5 M solution of n-butyllithium (6.1 eq). The mixture was stirred for 10 minutes. At the end of the period, a slurry of ester compound I (1 eq) in THF (14 ml/g of ester compound I) was cannulated into the performed Li—NHPr solution. The reaction mixture was warmed to 25° C. and stirred till all of ester compound I was consumed (~3 hours). After the reaction was judged to be completed by HPLC, the reaction mixture was cooled to ~0° C. and was slowly treated with acetic acid (5 ml/g of ester compound I). The slurry was then warmed to ~20° C. and was stirred for 1 hour. At the end of the period, the solvent was distilled under vacuum to the minimum volume and the concentrated slurry was diluted with a solution of acetone (10 ml/g of ester compound I) and water (20 ml/g of ester compound I). The slurry was stirred for 1 hour and was cooled to ~5° C. The slurry was filtered and the cake was washed with acetone (5 ml/g of ester compound I). The cake was dried to give the amide product II (typically in 85% yield and 99 AP).

Method B:

A solution of n-propylamine (20 eq) in 2,2,2-trifluoroethanol (10 ml/g of ester compound 1) was slowly treated with 2.5 M solution of n-butyllithium (1.5 eq). The mixture was stirred for 5 minutes. At the end of the period, the starting material, ester compound I, was added and the reaction mixture was warmed to 90° C. The reaction mixture was held at 90° C. for 24 hours and was allowed to cool to ~20° C. The reaction mixture was then analyzed by HPLC. Typically, analysis indicated there was only 1.57 AP of starting material left.

Method C:

A solution of n-propylamine (2 eq) in methylene chloride (10 ml/g of ester compound I) at 20° C. was slowly treated with 2.0 M solution of trimethylaluminum (4 eq) in hexanes. The mixture was stirred for 15 minutes. At the end of the period, the starting material, ester compound I (1 eq), was added and the reaction mixture was warmed to 60° C. The reaction mixture was held at 60° C. for 24 hours and was allowed to cool to ~20° C. The reaction mixture was then slowly quenched with aqueous HCl solution and analyzed by HPLC. Typically, analysis indicated there was 96.8 AP of amide compound II product with 0.03 AP of the dipropylamide impurity.

What is claimed is:

1. A process for preparing an amide of the structure

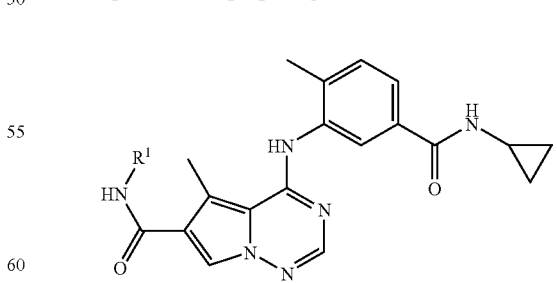

where $R^1$ is lower alkyl or aryl,
which comprises
a) providing a mixture of a strong organometallic base and an amine of the structure $R^1NH_2$ where $R^1$ is lower alkyl or aryl, in an organic solvent b) providing an ester of the structure

[structure: ethyl ester pyrrolotriazine with cyclopropyl benzamide, EtO₂C substituent]

in an organic solvent; and
c) reacting the step a) mixture and the ester of step b) to form the amide product.

2. The process as defined in claim 1 wherein the reaction is carried out at temperature within the range from about −10° to about 110° C.

3. The process as defined in claim 1 wherein the ester is provided as a suspension in an organic solvent.

4. The process as defined in claim 1 wherein the organic solvent employed for the strong organometallic base is tetrahydrofuran and the ester is in suspension with an organic solvent which is tetrahydrofuran.

5. The process as defined in claim 1 wherein the strong organometallic base is an alkyllithium.

6. The process as defined in claim 5 wherein the alkyllithium is hexyllithium or n-butyllithium.

7. The process as defined in claim 1 wherein the strong organometallic base is lithium hexamethyldisilazane, lithium diisopropylamide, sodium diisopropylamide or potassium diisopropylamide.

8. A process for preparing an amide of the structure which comprises

[structure: amide product with $R^1$-NH substituent]

wherein $R^1$ is alkyl or aryl, which comprises providing an ester of the structure

[structure: ethyl ester intermediate]

treating the ester with an amine of the structure $R^1NH_2$ wherein $R^1$ is alkyl or aryl, and an alkyllithium base, at a temperature within the range from about 10° to about 40° C. to form the amide.

9. The process as defined in claim 8 wherein the reaction is carried out in the presence of tetrahydrofuran as a solvent, the alkyllithium base is hexyllithium or n-butyllithium, and the amine is n-propylamine.

10. A process for preparing an amide of the structure

[structure: amide product with $R^1$-NH substituent]

wherein $R^1$ is alkyl or aryl, which comprises providing an ester of the strucutre

[structure: ethyl ester intermediate]

treating the ester with an amine of the structure $R^1NH_2$ in the presence of 2,2,2-trifluoroethanol and n-butyllithium or hexyllithium while maintaining the reaction at a temperature within the range from about 50° to about 120° C. to form the amide.

11. A process for preparing an amide of the structure

[structure: amide product with $R^1$-NH substituent]

which comprises providing an ester of the structure

[structure: ethyl ester intermediate]

wherein $R^1$ is alkyl or aryl,
treating the ester with an amine of the structure $R^1NH_2$ and trimethylaluminum while maintaining the reaction at a temperature with the range from about 40° to about 80° C. to form the amide.

* * * * *

UNITED STATES PATENT AND TRADEMARK OFFICE
CERTIFICATE OF CORRECTION

| | | |
|---|---|---|
| PATENT NO. | : 7,148,348 B2 | Page 1 of 1 |
| APPLICATION NO. | : 11/199746 | |
| DATED | : December 12, 2006 | |
| INVENTOR(S) | : Reginald O. Cann et al. | |

It is certified that error appears in the above-identified patent and that said Letters Patent is hereby corrected as shown below:

In the Claims:

Claim 10:

Column 26, line 17, change "strucutre" to -- structure --.

Claim 11:

Column 26, line 64, change "with" to -- within --.

Signed and Sealed this
Ninth Day of October, 2012

David J. Kappos
*Director of the United States Patent and Trademark Office*